US008434232B2

(12) United States Patent
Jones, III et al.

(10) Patent No.: US 8,434,232 B2
(45) Date of Patent: May 7, 2013

(54) METHOD FOR CONSTRUCTING A TRUSS FROM SELECTED COMPONENTS

(75) Inventors: John E. Jones, III, Seattle, WA (US); Benjamin C. Donner, Federal Way, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 444 days.

(21) Appl. No.: 12/492,546

(22) Filed: Jun. 26, 2009

(65) Prior Publication Data

US 2010/0326005 A1    Dec. 30, 2010

(51) Int. Cl.
*B21D 47/00* (2006.01)
(52) U.S. Cl.
USPC ........... 29/897.31; 29/897; 29/897.3; 52/633; 52/643; 73/73; 702/33; 702/155
(58) Field of Classification Search ............... 29/897, 29/897.3, 897.31; 73/73, 760, 866; 702/33, 702/81, 155, 159, 183, 189; 52/642
See application file for complete search history.

(56) References Cited

U.S. PATENT DOCUMENTS

| | | | |
|---|---|---|---|
| 3,991,535 A * | 11/1976 | Keller et al. | ..................... 52/642 |
| 4,852,029 A | 7/1989 | Pope et al. | |
| 4,932,173 A | 6/1990 | Commins | |
| 4,964,060 A * | 10/1990 | Hartsog | ............................ 703/1 |
| 5,361,495 A | 11/1994 | Pyle | |
| 5,560,156 A | 10/1996 | McDonald | |
| 5,609,403 A | 3/1997 | Bell | |
| 6,295,544 B1 | 9/2001 | Cheung | |
| 6,305,224 B1 | 10/2001 | Stanish | |
| 7,017,413 B2 | 3/2006 | Floyd | |
| D518,359 S | 4/2006 | Bronson | |
| 7,286,956 B2 * | 10/2007 | Floyd et al. | ................... 702/159 |
| 7,324,904 B2 | 1/2008 | Floyd | |
| 7,383,730 B2 | 6/2008 | Huang | |
| 2007/0137323 A1 | 6/2007 | Floyd | |

FOREIGN PATENT DOCUMENTS

CA    2590435    5/2007

OTHER PUBLICATIONS

The Encyclopedia of Trusses published by Alpine Engineered Products Inc. and available at http://www.alpeng.com/images/stories/pdfs/EOT.pdf.
Lischkoff, James, Truss Uplift: Cause and Cures, Progressive Builder, Jul. 1985.
Forinteck Canada Corp, CMHC 1989 External Research Program Project Uplift of Wood Trusses Atlantic Canada CR File: 6585/H9-3.
Onysko, et al., Forinteck Canada Corp, Seasonal Uplift of Roof Trusses: A Progress Report.

* cited by examiner

*Primary Examiner* — Richard Chang
(74) *Attorney, Agent, or Firm* — Christensen O'Connor Johnson Kindness PLLC

(57) ABSTRACT

A method for constructing a truss includes selecting three or more chord elements (two or more upper chord elements and one or more lower chord elements) and one or more web elements. The selecting of the components includes estimating a first change in length for each of the two or more upper chord elements and estimating a second change in length of each of the one or more lower chord elements, the first change in length and the second change in length in response to changes in conditions to which the truss is exposed. The one or more web elements are selected from the plurality of wood members to compensate for the deformation caused by the first change in length and the second change in length.

16 Claims, 6 Drawing Sheets

METHOD FOR CONSTRUCTING A TRUSS FROM SELECTED COMPONENTS

TECHNICAL FIELD

The present disclosure is directed generally to trusses and methods for selecting components for constructing truss structures.

BACKGROUND

Trusses are pre-manufactured structural roof components which support the roofing and carry the top floor ceilings. Wood trusses are widely used in single and multi-family residential, institutional, agricultural and commercial construction. Their high strength-to-weight ratios permit long spans, offering greater flexibility in floor plan layouts. They can be designed in almost any shape or size, restricted only by manufacturing capabilities, shipping limitations and handling considerations.

FIG. 1 shows an example of a standard truss known to those of ordinary skill in the art as a Howe truss. The truss 100 is made from three primary components: upper chord elements 102, web elements 104, and a lower chord element 106. The lower chord element 106 is arranged horizontally so that it is adjacent to a ceiling structure, which is represented by a reference line 108. The upper chord elements 102 and the lower chord element 106 are connected end-on-end to form an enclosed structure and the web elements 104 are arranged inside the enclosed structure. The upper chord elements 102, the web elements 104, and the lower chord element 106 are typically made from dimensional lumber and may be connected with interlocking structures, nails, metal plates, or other types of connections.

A common problem associated with trusses made from wood is a phenomenon known as trust uplift. Truss uplift is a deformation of the truss structure, normally caused by a moisture differential between the lower chord element 106 and the upper chord elements 102. Because wood is a hygroscopic material, it can expand and contract due to changes in temperature and/or humidity, resulting in a change in length of the truss components. FIG. 2 shows an example of the truss 100 from FIG. 1 after the components have expanded as a result of exposure to a moisture and/or temperature change. In most roof construction applications, the lower chord element 106 is buried in heavy insulation, which keeps it relatively dry and warm in the winter when the rest of the truss 100 is exposed to a higher relative humidity environment of cold air and moisture. As a result, the upper chord elements 102 and the web elements 104 expand, but the length of the lower chord element 106 remains relatively stable. This results in a change in distance between the lower chord element 106 and the upper chord elements 102. In FIG. 2, the degree of uplift is schematically shown by reference character 110. The greatest amount of uplift is often seen at the center of the truss.

Conditions contributing to uplift may include rain, wind, seasonal changes, or other factors influencing the moisture content of each truss component. In addition, components of truss structures may also be exposed to moisture changes during transportation or construction. Over time, the resulting dimensional changes of the truss components can lead to significant deformation of the overall truss structure. In a residential construction application, the lower chord element 106 often lifts in the winter and lowers again in the spring. When trusses arch up, they take the dry wall and ceiling with them, which can cause visible cracking. As the trusses dry out with the warm summer air, they can drop back down closing most of the cracks. This cracking is upsetting to a homeowner, as most homeowners might assume that there are structural problems with the house.

Both the wood products industry and the construction industry have taken steps to minimize truss uplift and other problems associated with the expansion or shrinkage of truss components. One solution is to avoid connecting the truss directly to the wall partitions. Instead the builder can connect the truss with an 'L' bracket (known as a "truss clip") or strap, which allows vertical movement of the truss. An example of this solution is described in U.S. Pat. No. 5,560,156 and U.S. Pat. No. D318,359, which are hereby incorporated by reference. Another technique commonly practiced by wood products manufacturers is to grade lumber according to its strength and select only the strongest lumber to be sold as the upper chord elements 102 and the lower chord elements 106. Although the purpose of this lumber selection technique relates primarily to strength, selecting stronger chord elements may also reduce uplift.

One drawback of known solutions for truss uplift is that many of them involve alterations to the construction of the house. Additionally many are remedial in nature as opposed to preventative. Therefore, the wood product manufacturer has very little control over the perceived performance of the products sold for truss construction. Thus, there is a need to develop a new method that enables wood product manufacturers to select components for constructing trusses with minimized susceptibility to uplift.

SUMMARY

The following summary is provided for the benefit of the reader only and is not intended to limit in any way the invention as set forth by the claims. The present disclosure is directed generally towards truss structures and methods for constructing truss structures.

In one embodiment, a sample of lumber is provided and measurements are conducted to predict a value representing dimensional instability (e.g., predicted percent shrinkage rate, coefficient of hygroscopic expansion, coefficient of thermal expansion, estimated change in length) for each piece in the lumber sample. Accordingly, a distribution of the values representing dimensional instability for the sample of lumber is generated. The deformation of truss shape due to dimensional instability may be evaluated using models (e.g., finite element models, geometric models, static deflection analysis). Alternatively, empirical measurements can be made of truss deformation due to dimensional instability. Models according to embodiments of the disclosure may be used to determine a threshold for a value representing dimensional instability based on minimizing truss uplift. Lumber in the sample having a value representing dimensional instability below the threshold value is selected and lumber having a value representing dimensional instability above the threshold value is either diverted for use in other wood products or scrapped.

In other embodiments, lumber for the web elements may be selected using a model to determine an optimal value representing dimensional instability for the web elements based on the predicted change in length of the chord elements. In one embodiment, the distribution mentioned above is divided into three ranges: a first range, a second range, and a third range. Lumber within the second range generally has a higher value representing dimensional instability than lumber within the first range. Lumber within the third range generally has a higher value representing dimensional instability than lumber within the second range. In some embodiments, the web elements are selected from the lumber in the second range, the chord elements are selected from the lumber in the first range, and the lumber within the third range is scrapped or diverted. In some embodiments, the first range, the second range, and the third range are all different. In some embodiments, there may be some degree of overlap between the ranges.

In yet another embodiment, the distribution mentioned above is divided into four ranges: a first range, a second range, a third range, and a fourth range. Lumber within the first range generally has the lowest value representing dimensional instability and lumber within the fourth range generally has the highest value representing dimensional instability. Lumber within the third range generally has a higher value representing dimensional instability than lumber in the fourth range. In some embodiments, the web elements are selected from the lumber in the third range, the chord elements are selected from the lumber in the first range, and the lumber within the second and fourth ranges is scrapped or diverted. In some embodiments, the first range, the second range, the third range, and the fourth range are all different. In some embodiments, there may be some degree of overlap between the ranges.

Further aspects are directed towards trusses constructed using methods described in the disclosure. Embodiments of a truss structure according to the disclosure are enclosed structures made from two or more upper chord elements and one or more lower chord elements. The two or more upper chord elements and the one or more lower chord elements may be arranged in a single plane and connected end-on-end to form an inverted V structure. One or more web elements may be arranged inside the enclosed structure and connected to the chord elements. In embodiments according to the disclosure, the one or more web elements have values representing dimensional instability that are lower, on average, than the values representing dimensional instability for the two or more upper chord elements.

BRIEF DESCRIPTION OF THE DRAWINGS

The present disclosure is better understood by reading the following description of non-limitative embodiments with reference to the attached drawings wherein like parts of each of the figures are identified by the same reference characters, and are briefly described as follows.

DETAILED DESCRIPTION

Figure 1:
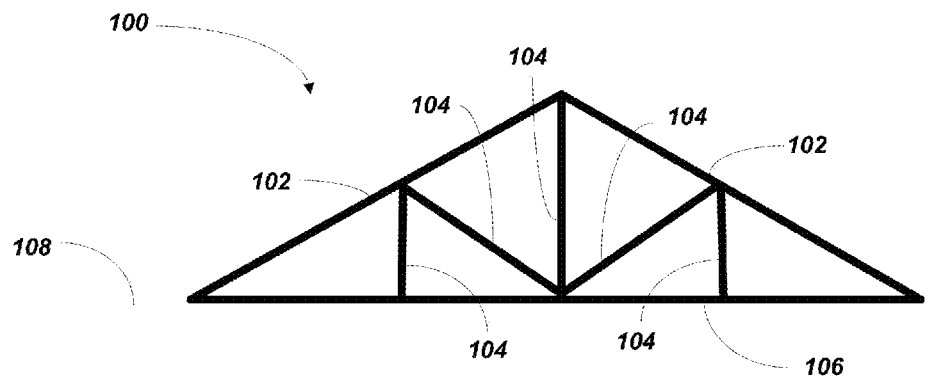
FIG. 1 is a schematic view of a Howe truss.
Figure 2:
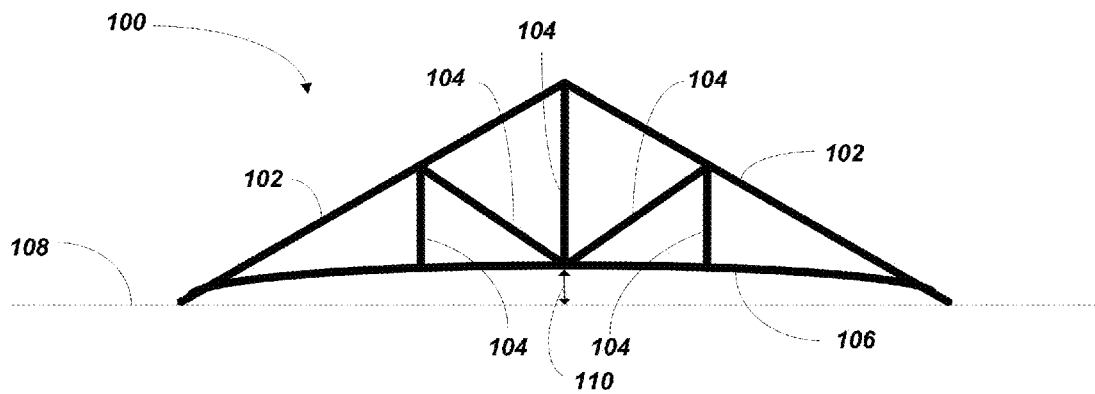
FIG. 2 is a schematic view of the truss from FIG. 1 after undergoing dimensional changes resulting in uplift.

The present disclosure describes truss structures and methods for selecting elements for constructing truss structures. Certain specific details are set forth in the following description and FIGS. 1-11 to provide a thorough understanding of various embodiments of the disclosure. Well-known structures, systems, and methods often associated with such systems have not been shown or described in details to avoid unnecessarily obscuring the description of various embodiments of the disclosure. In addition, those of ordinary skill in the relevant art will understand that additional embodiments of the disclosure may be practiced without several of the details described below.

In this disclosure, the term "wood" is used to refer to any organic material produced from trees, shrubs, bushes, grasses or the like. The disclosure is not intended to be limited to a particular species or type of wood. The term "chord elements" is used to refer to the outer members forming an enclosed structure for any type of truss configuration. The term "web elements" is used to refer to inner members arranged within the truss. The term "coefficient of expansion" is used to refer to dimensional change (e.g., shrinking or expansion) of a wood member due to a change in a condition to which the wood member is exposed. The condition may relate, for example, to changes in moisture, changes in relative humidity, changes in temperature, or any other variable which may affect the dimensions of a wood member. Equation 1 represents an expansion coefficient ($\epsilon$) where L is the length of the wood member and V is a variable representing a condition to which the wood member is exposed.

$$\varepsilon \equiv \frac{1}{L_0} \frac{\partial L}{\partial V} \qquad \text{Equation 1}$$

As stated above, the variable V may relate to any condition which may affect the dimensions of the wood member. For example, if the variable is moisture, $\epsilon$ may be referred to as a hygroscopic expansion coefficient. If the variable is temperature, $\epsilon$ may be referred to as a thermal expansion coefficient.

Methods according to the disclosure involve strategies for selecting truss components (e.g., the upper chord elements 102, the web elements 104, and the lower chord element 106) from a sample of lumber pieces. According to embodiments of the disclosure, the first step involves predicting dimensional instability of each piece of lumber in the sample. Some methods for predicting dimensional instability are described, for example, in U.S. Pat. No. 6,305,224, U.S. Pat. No. 7,017,413, U.S. Pat. No. 7,324,904, and U.S. Pat. No. 7,383,730, which are hereby incorporated by reference. In addition, other methods for predicting dimensional instability known to those of ordinary skill in the art may be used. Dimensional instability may be quantified as change in length, percent shrinkage, coefficient of hygroscopic expansion, coefficient of thermal expansion, or any other measure of dimensional instability known to one of ordinary skill in the art.

In some embodiments of the disclosure, the next step involves constructing a model of truss deformation given the lengths or length-changes of each truss member under a set of conditions. Models according to the disclosure may be used to guide selection of the lumber pieces from the sample. There are many different shapes and configurations for truss structures, and models may vary based on the geometry of the truss being constructed. An example of truss configurations may be found in *The Encyclopedia of Trusses* published by Alpine Engineered Products Inc. and available at http://www.alpeng.com/images/stories/pdfs/EOT.pdf. In addition, models according to the disclosure may also be based on other truss configurations known to those of ordinary skill in the art.

Figure 3:
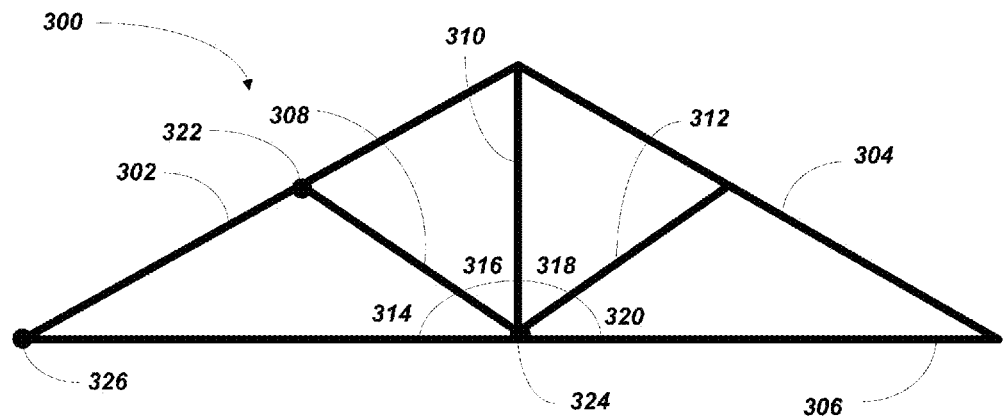
FIGS. 3 and 4 are examples of a model of a truss according to embodiments of the disclosure.
Figure 4:
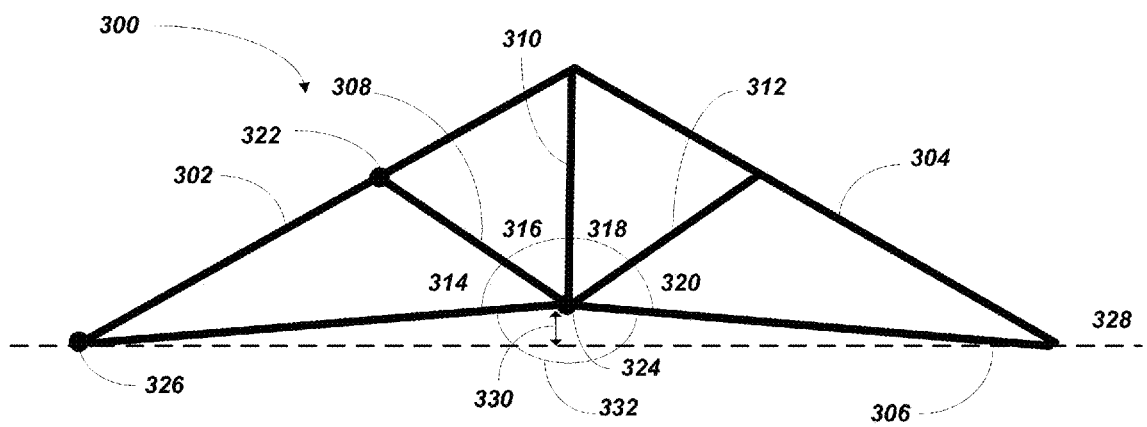

FIGS. 3 and 4 illustrate an example of a model according to embodiments of the disclosure. FIG. 3 includes a truss 300 having a first chord element 302, a second chord element 304, and a third chord element 306 arranged in a triangular shape; and a first web element 308, a second web element 310, and a third web element 312 arranged inside the first, second, and third chord elements 302, 304, and 306. The third chord element 306 and the first web element 308 intersect to form a first angle 314. The first web element 308 and the second web element 310 intersect to form a second angle 316. The second web element 310 and the third web element 312 intersect to form a third angle 318. The third web element 312 and the third chord element 306 intersect to form a fourth angle 320. The truss 300 illustrated in FIG. 3 is known to those of ordinary skill in the art as a modified Howe truss or a Fan truss. Although FIGS. 3 and 4 illustrate a wood truss, trusses may be constructed from various materials (e.g. metal, composites) and methods according to the disclosure may be applied regardless of the truss material.

FIG. 3 illustrates the truss 300 in an initial state where each component has an initial moisture content. The initial moisture content of the chord elements 302, 304, and 306 may be the same as the initial moisture content of the web elements 308, 310, and 312. Additionally, each element may have a different initial moisture content.

FIG. 4 illustrates the truss 300 after a change in a condition (e.g., moisture, temperature, relative humidity) resulting in an expansion of the first chord element 302 and the second chord element 304. The first chord element 302 and the second chord element 304 may undergo the same degree of expansion or varying degrees of expansion. In FIG. 4, the truss 300 is arranged on a reference line 328 to illustrate uplift as indicated by reference character 330.

According to embodiments of the disclosure, the uplift at various locations on the truss 300 can be calculated given the length of the truss components. In this example, truss uplift is calculated with respect to the center web element (the second web element 310); however, numerous other calculations are envisioned within the scope of this disclosure. Although this example illustrates a truss having a relatively simple geometry and a geometric model is used, models according to embodiments of the disclosure may also be constructed for more complicated truss structures. In addition, models according to embodiments of the disclosure may be modified to include dead loads and live loads acting as forces on the truss structure. Accordingly, many different types of models may be used to evaluate expansion. Geometric models, finite element analysis, static deflection analysis, or any other method known to those of ordinary skill in the art may be applied to create more sophisticated models according to the disclosure.

Referring back to FIG. 3 and FIG. 4, Euclidean geometry formulas may be used to calculate the uplift 330 for the truss 300. According to the law of cosines, the first angle 314 may be calculated given the lengths of the truss components forming a triangle defined by a first point 322, a second point 324, and a third point 326, according to Equation 2.

$$\theta = \cos^{-1}\left(\frac{L_1^2 + L_2^2 - L_3^2}{2L_1 L_2}\right) \quad \text{Equation 2}$$

In Equation 2, $\theta$ is the first angle 314, $L_1$ is the distance between the point first point 322 and the third point 326, $L_2$ is the distance between the second point 324 and the third point 326, and $L_3$ is the distance between the first point 322 and the second point 324. The second angle 316, the third angle 318, and the fourth angle 320 may be calculated according to the same procedure. The sum of the first angle 314, the second angle 316, the third angle 318, the fourth angle 320, and a fifth angle 332 (also known as the "lift angle") around the second point 324 should equal 360 degrees. Thus, the fifth angle 332 can be calculated according to Equation 3:

$$\lambda = 2\pi - (\theta + \phi + \psi + \sigma) \quad \text{Equation 3}$$

In Equation 3, $\theta$ is the first angle 314, $\phi$ is the second angle 316, $\psi$ is the third angle 318, $\sigma$ is the fourth angle 320, and $\lambda$ is the fifth angle 332. Once $\lambda$ is known, the uplift at the second point 324 may be calculated according to Equation 4:

$$\text{Uplift} = L_2 \cdot \cos\left(\frac{\lambda}{2}\right) \quad \text{Equation 4}$$

In Equation 4, $\lambda$ is the fifth angle 332 and $L_2$ is the distance between the point first point 324 and the third point 326. Using this model, the impact of changes in the lengths of various truss components resulting from a change in a condition affecting the dimensions of the truss 300 may be evaluated. If a wood products manufacturer has a sample of lumber with known or estimated expansion properties, models can be used to estimate the resulting uplift under a given set of conditions or a change in conditions for truss constructions using various configurations of different pieces of lumber. Accordingly, the wood manufacturer may select pieces of lumber for the web elements (308, 310, and 312) which compensate for the change in length of the chord elements (302, 304, and 306), thereby minimizing uplift of the truss 300.

Figure 5:
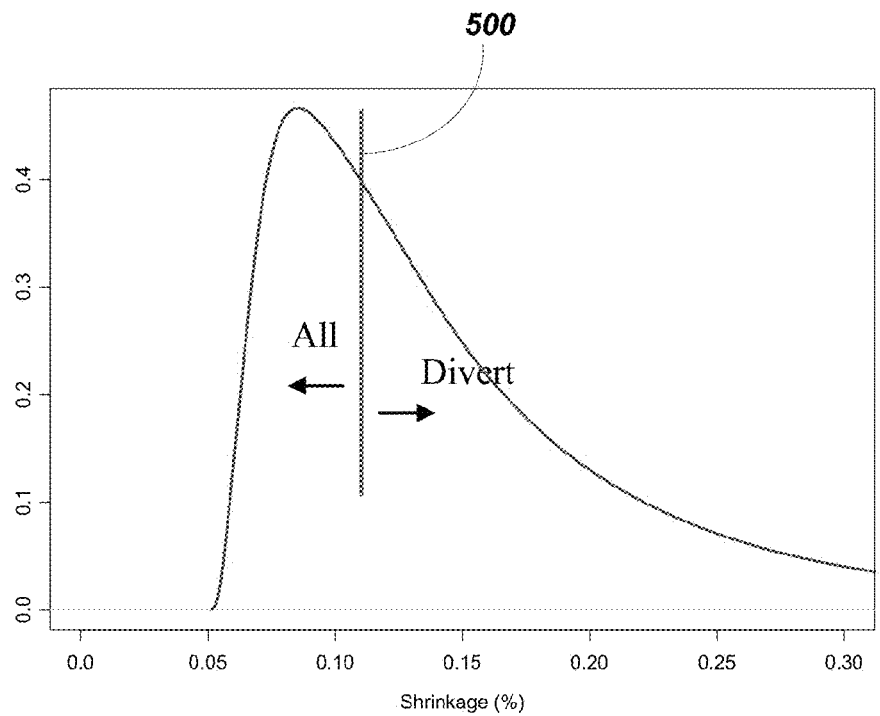
FIG. 5 is a graphical depiction of a method for selecting components for truss construction according to embodiments of the disclosure.
Figure 6:
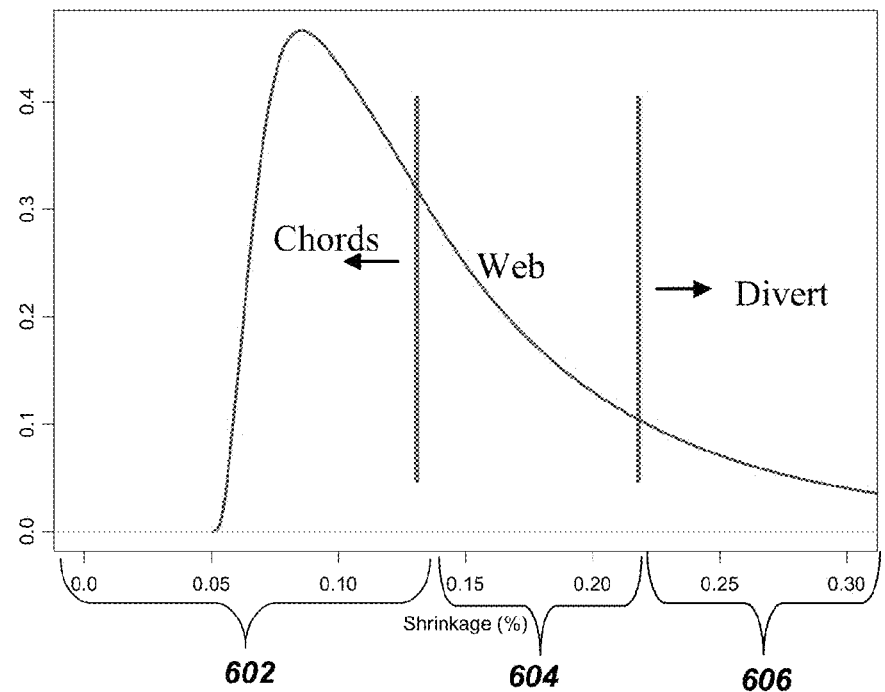
FIG. 6 is a graphical depiction of another method for selecting components for truss construction according to embodiments of the disclosure.
Figure 8:
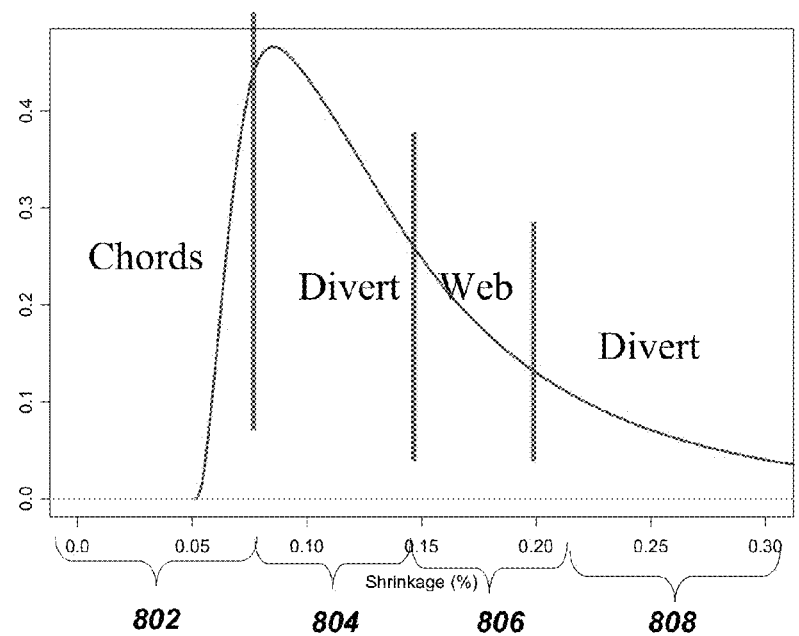
FIG. 8 is a graphical depiction of yet another method for selecting components for truss construction according to embodiments of the disclosure.

Models according to the disclosure may be used to establish selection criteria for truss components from a given sample of lumber. FIGS. 5, 6, and 8 are graphical depictions of methods for selecting components for truss construction according to embodiments of the disclosure. One of ordinary skill in the art will appreciate that the methods described in FIGS. 5, 6, and 8 may be used for selecting components for construction of various truss configurations and are not limited to the configurations explicitly illustrated in the examples.

FIG. 5 shows a plot of the probability density function of estimated values representing dimensional instability for a population of lumber. In this example, the percent shrinkage rate when the moisture content of the lumber changes from about 65% relative humidity to about 20% relative humidity is used; however other values representing changes in different conditions may be used instead (e.g., temperature, relative humidity). One of ordinary skill in the art will appreciate that embodiments of the disclosure may involve plots of probability density functions or other statistical distributions relating to different changes in moisture content or other variables. The values for predicted percent shrinkage may be obtained by estimating dimensional instability as described earlier in the disclosure.

In this example, all lumber having a predicted percent shrinkage below a threshold value indicated by a line 500 is selected for truss construction. The lumber selected may be used for either the chord elements or the web elements of a truss. Generally half of the lumber may be selected while the other half is diverted or scrapped. Those of ordinary skill in the art will appreciate that the line 500 is merely an example of a threshold value and that other values may be used. The lumber pieces having a predicted percent shrinkage rate higher than the threshold value may be diverted for use in producing other wood products or scrapped. The threshold value is based on using models according to embodiments of the disclosure to predict uplift when components having varied predicted shrinkage rates within the population are selected.

FIG. 6 illustrates another example of methods for selecting truss components according to embodiments of the disclosure. In this example, the same probability density function from FIG. 5 is shown divided into three ranges: a first range 602, a second range 604, and a third range 606. In some embodiments, lumber from the first range 602 is selected for the chord elements, lumber within the second range 604 is selected for the web elements, and lumber within the third range 606 is diverted or scrapped. The lumber selected for the web elements generally has a higher predicted percent shrinkage rate than the lumber selected for the chord elements. In other words, using lumber for the web elements that is generally less dimensionally stable than the lumber selected for the chord elements may minimize uplift according to some models. Generally the chord elements may be selected from the top ⅔ of the lumber population ranked according to lowest predicted shrinkage rate. The next 23% may be used for the web elements, while the remainder (approximately 10%) is diverted or scrapped.

Figure 7:
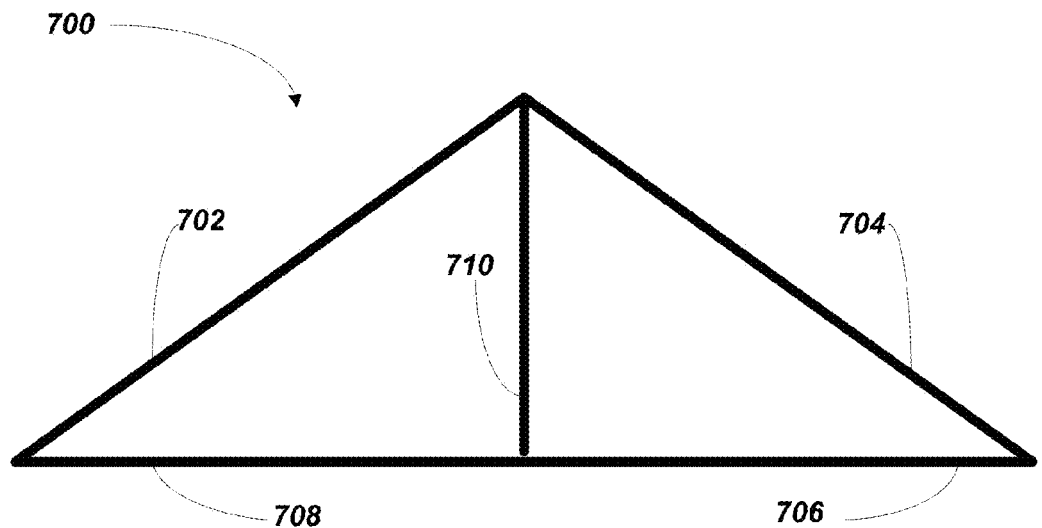
FIG. 7 is a schematic of a King Post truss.

In some embodiments, lumber for the web elements is selected based on its ability to compensate for the predicted shrinkage of lumber selected for the chord elements. FIG. 7 illustrates an example of this using a King Post truss 700 which is constructed from five components: a first upper chord element 702, a second upper chord element 704, a first lower chord element 706, a second lower chord element 708, and a web element 710. Using models according to embodiments of the disclosure, one may calculate an optimal coefficient of hygroscopic expansion for the web element 710 given a predicted coefficient of hygroscopic expansion for the first upper chord element 702 assuming that the length of the second lower chord element 708 remains relatively stable. For the King Post truss 700, Equation 5 may be used to calculate the optimum coefficient of hygroscopic expansion $\varepsilon_3$ for the web element 710.

$$\varepsilon_3 = \sqrt{\frac{[L_{2,0}(1+\varepsilon_2)]^2 - L_1^2}{L_{3,0}^2}} - 1 \qquad \text{Equation 5}$$

In Equation 5, $\varepsilon_2$ is the coefficient of hygroscopic expansion for the first upper chord element 702, $L_1$ is the length of the second lower chord element 708, $L_{2,0}$ is the initial length of the first upper chord element 702, and $L_{3,0}$ is the initial length of the web element 710. By repeating this method for numerous components of multiple trusses, one can derive a table showing the optimal coefficient of hygroscopic expansion for the web element 710 based on a given coefficient of hygroscopic expansion for the first upper chord element 702. Table 1 is an example of such a table.

TABLE 1

Optimal pairs of hygroscopic expansion coefficients of upper chords and center webs in a King Post truss.

| Upper Chord $\varepsilon$ | Optimal Center Web $\varepsilon$ |
| --- | --- |
| 0.0005 | 0.0085 |
| 0.0006 | 0.010 |

TABLE 1-continued

Optimal pairs of hygroscopic expansion coefficients of upper chords and center webs in a King Post truss.

| Upper Chord $\varepsilon$ | Optimal Center Web $\varepsilon$ |
| --- | --- |
| 0.0007 | 0.012 |
| 0.0008 | 0.0135 |

Although Equation 5 and Table 1 illustrate methods according to embodiments of the disclosure with respect to a King Post truss, similar methods may be applied to the various other truss configurations. Thus, different optimal pairs may be obtained. In addition, pairings may be made with respect to coefficient of expansion other than the coefficient of hygroscopic expansion (e.g., coefficient of thermal expansion).

FIG. 8 illustrates another example of methods for selecting truss components according to embodiments of the disclosure. In this example, the same probability density function from FIG. 5 is shown divided into four ranges: a first range 802, a second range 804, a third range 806, and a fourth range 808. In some embodiments, lumber from the first range 802 is selected for the chord elements, lumber within the second range 804 is diverted or scrapped, lumber within the third range 806 is selected for the web elements, and the lumber from the fourth range 808 is diverted or scrapped. Here the expansion of the web elements is selected to match the expansion of the chord elements, thereby minimizing uplift.

In addition to the methods described above, the disclosure also relates to trusses constructed using methods described in the disclosure. Embodiments of a truss structure according to the disclosure include enclosed structures made from two or more upper chord elements and one or more lower chord elements. The two or more upper chord elements and the one or more lower chord elements may be arranged in a single plane and connected end-on-end to form an inverted V structure. One or more web elements may be arranged inside the enclosed structure and connected to the chord elements. In embodiments according to the disclosure, the one or more web elements have values representing dimensional instability that are lower than the values representing dimensional instability for the two or more upper chord elements. The values representing dimensional instability may be, for example, a coefficient of expansion. In some embodiments, the one or more web elements have values representing dimensional instability that are higher than the values representing dimensional instability for the one or more lower chord elements.

Figure 9:
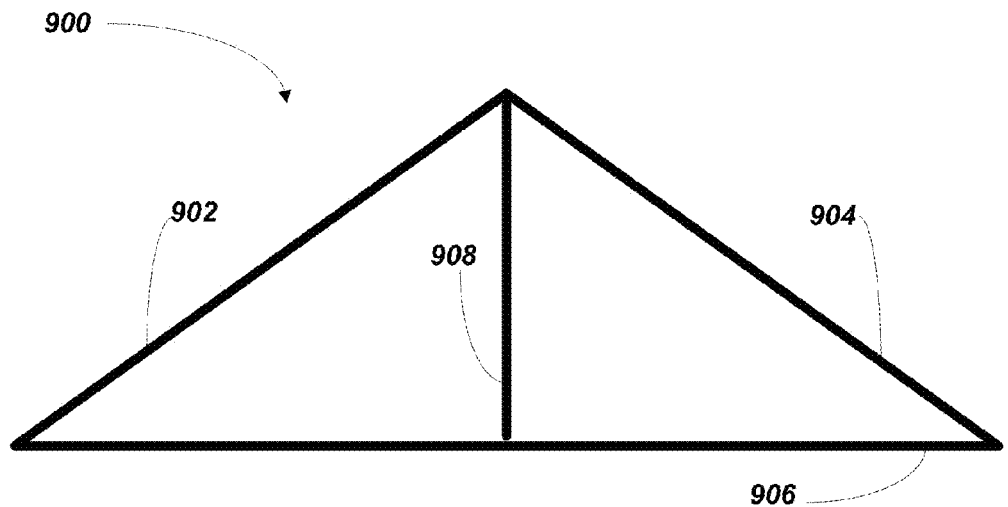
FIG. 9 is an example of a truss constructed according to embodiments of the disclosure.

FIG. 9 shows an example of a truss according to embodiments of the disclosure. The truss 900 includes four elements: a first chord element 902, a second chord element 904, a third chord element 906, and a web element 908. The coefficient of hygroscopic expansion for the web element 908 is higher than the coefficient of hygroscopic expansion for the first chord element 902 and the coefficient of hygroscopic expansion for the second chord element 904. In this example, the length of the third chord element 906 is assumed to remain relatively stable; however, in some embodiments the length of the third chord element 906 may change. Although FIG. 9 shows one example of a geometrically simple truss, trusses according to embodiments of the disclosure may have different numbers of components arranged in different configurations.

In a roof structure made with trusses according to embodiments of the disclosure, the one or more web elements have values representing dimensional instability that are higher, on average, than the values representing dimensional instability for the two or more upper chord elements. In some embodiments, the one or more web elements have values representing dimensional instability that are higher, on average, than the values representing dimensional instability for the one or more lower chord elements. Roof structures made according to some embodiments of the disclosure are expected the exhibit less uplift than trusses made from randomly selected lumber. In addition, selecting lumber in accordance with some methods within the scope of the disclosure may improve truss stability while at the same time maximizing utilization of lumber having properties which are perceived to be undesirable for truss construction.

From the foregoing, it will be appreciated that the specific embodiments of the disclosure have been described herein for purposes of illustration, but that various modifications may be made without deviating from the disclosure. For example, methods according to embodiments of the disclosure may be used to construct truss configurations not explicitly illustrated in the disclosure. In addition, the ranges shown in FIGS. 5, 6, and 8 are merely examples. Different ranges may be appropriate based on the shape of the trusses and the available lumber. Accordingly, different models of truss expansion may also be used.

Aspects of the disclosure described in the context of particular embodiments may be combined or eliminated in other embodiments. For example, methods illustrated in FIG. 6 may be combined with methods illustrated for example, in FIG. 8. Further, while advantages associated with certain embodiments of the disclosure may have been described in the context of those embodiments, other embodiments may also exhibit such advantages, and not all embodiments need necessarily exhibit such advantages to fall within the scope of the disclosure. Accordingly, the invention is not limited except as by the appended claims.

The following example will serve to illustrate aspects of the present disclosure. The examples are intended only as a means of illustration and should not be construed to limit the scope of the disclosure in any way. Those skilled in the art will recognize many variations that may be made without departing from the spirit of the disclosure.

Example

A simulation study was conducted to compare the distribution of truss uplift calculations for four different truss member selection strategies. Strategy A simply involved random placement of mill-run lumber into the truss design. Strategies B, C, and D are all examples of methods according to embodiments of the disclosure.

The first step for the simulation study involved predicting the dimensional instability of a population of lumber pieces from which truss components will be selected. In this example, the lumber included 56 pieces having nominal dimensions of 2 inches by 4 inches by 16 inches from Plymouth, N.C. The dimensional instability of each piece of lumber was assessed by measuring the initial length, length change, and moisture content of each piece when moved from a 65% relative humidity equilibrium condition to a 20% relative humidity equilibrium condition. Equation 6 shows the formula used for calculating $\varepsilon$, the linear coefficient of hygroscopic expansion:

$$\varepsilon \equiv \frac{L_{65} - L_{20}}{M_{65} - M_{20}} \frac{1}{L_{65}} \qquad \text{Equation 6}$$

In Equation 6, $L_{65}$ is the length at 65% relative humidity. $L_{20}$ is the length at 20% relative humidity. $M_{65}$ is the moisture content at 65% relative humidity. $M_{20}$ is the moisture content at 20% relative humidity.

Figure 10:
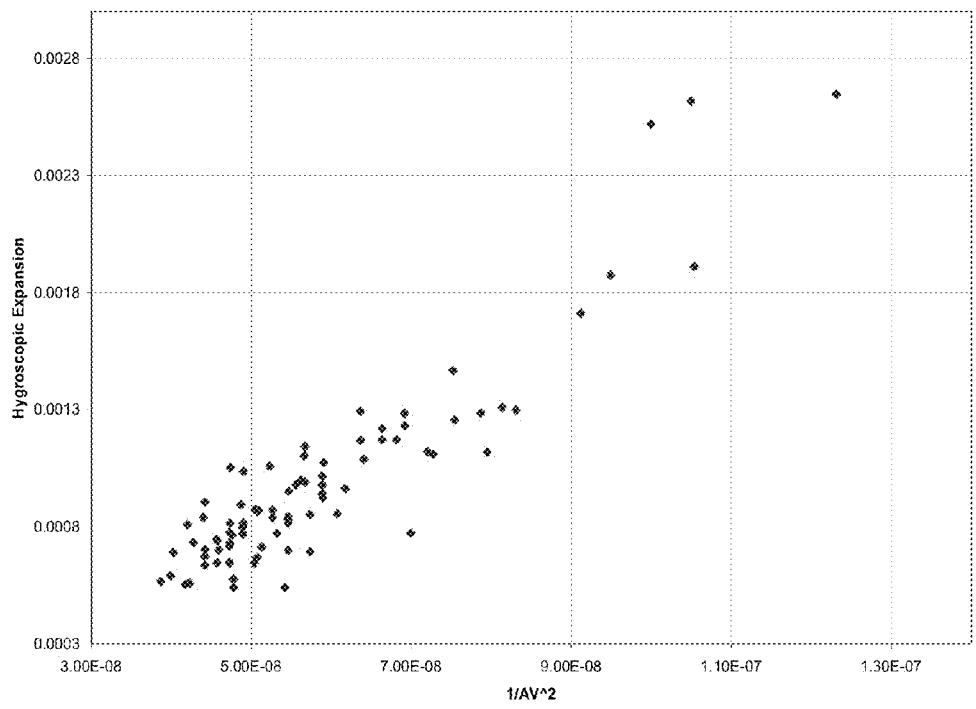
FIG. 10 is a graph showing the relationship between coefficients of hygroscopic expansion and acoustic velocity.

Prediction models of dimensional instability were developed based on measures of acoustic velocity using methods known to those of ordinary skill in the art. Examples of methods used are described, for example, in U.S. Pat. No. 7,017,413. FIG. 10 is a graph of the coefficients of linear hygroscopic expansion plotted against the inverse square of acoustic velocity.

The next step involved generating a distribution of computed truss uplifts based on selecting components for trusses using methods according to embodiments of the disclosure. Strategy B involved selecting truss components according to an example of embodiments described in FIG. 5. In this example, the chosen threshold value was about 0.12%. Thus, only lumber pieces having a predicted percent shrinkage rate below about 0.12% were selected.

Strategies C and D involved evaluating models according to embodiments of the disclosure to determine the optimum placement of components in a modified Howe truss structure (see FIGS. 3 and 4 for an example of a modified Howe truss). Strategy C involved selecting truss components according to an example of embodiments described in FIG. 6. In this example, all of the lumber pieces having a predicted coefficient of linear hygroscopic expansion below about 0.08% were selected for the chord elements. All of the lumber pieces having a predicted coefficient of linear hygroscopic expansion between about 0.08% and about 0.22% were selected for the web elements. The lumber pieces having a predicted coefficient of linear hygroscopic expansion higher than about 0.22% were scrapped or diverted.

Strategy D involved selecting truss components according to an example of embodiments described in FIG. 8. In this example, all of the lumber pieces having a predicted coefficient of linear hygroscopic expansion less than about 0.08% were selected for the chord elements. All of the lumber pieces having a predicted coefficient of linear hygroscopic expansion between about 0.15% and about 0.20% are used for the web elements. The lumber pieces having a predicted coefficient of linear hygroscopic expansion between about 0.08% and 0.15%, and above 0.20% were either scrapped or diverted.

Figure 11:
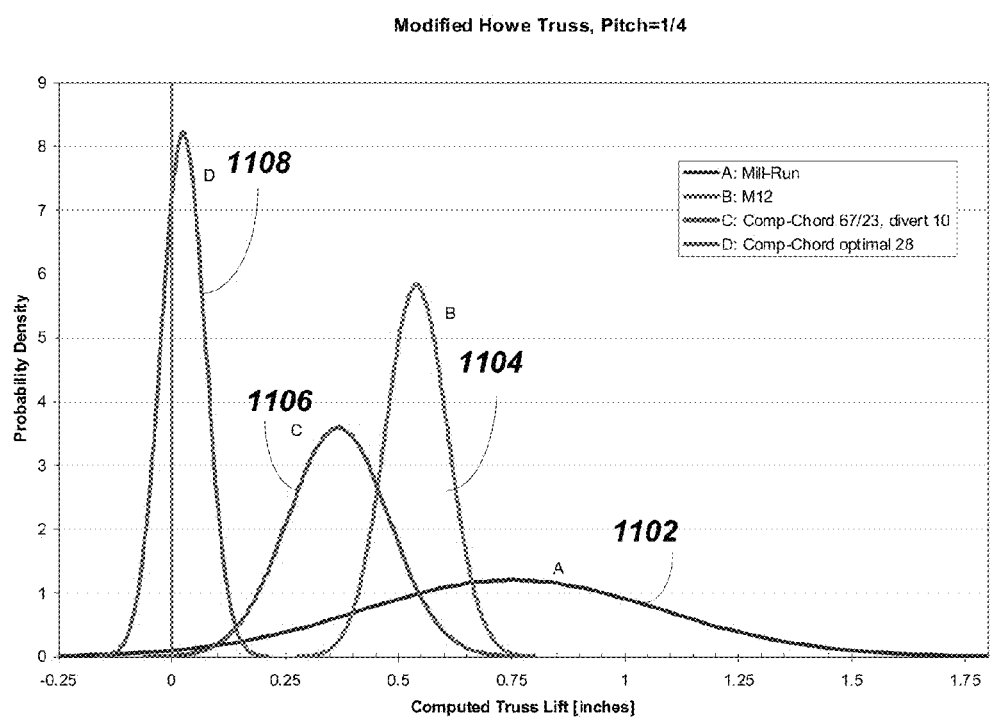
FIG. 11 is a graph illustrating computed truss lifts for simulated trusses made according to embodiments of the disclosure.

An algorithm was used to generate distribution plots of resulting truss uplifts for each strategy. FIG. 11 shows the resulting plot with 1102 representing the distribution for strategy A, 1104 representing the distribution for strategy B, 1106 representing the distribution for strategy C, and 1108 representing the distribution for strategy D. A pre-requisite for this algorithm is an estimated probability distribution for lumber linear hygroscopic expansion from which to simulate random selection of boards for the truss design. In this example, $F_{out}$ was used to represent the distribution from which the chord elements were selected; $F_{in}$ was used to represent the distribution from which the web elements were selected. For example, in strategy C, $F_{out}(e)$ is taken to be $Pr(\epsilon < e | \hat{\epsilon} < t)$, where $\hat{\epsilon}$ is the predicted coefficient of hygroscopic expansion and t is the sort threshold. $F_{out}$ and $F_{in}$ can be estimated from data using a number of statistical methods. An example of such an algorithm is described below. An alternative algorithm could involve replacing steps 4-6 with calculations from a finite element model.

1. Randomly select linear hygroscopic expansion values, $\epsilon_i$, from $F_{out}$ for all chord elements.
2. Randomly select linear hygroscopic expansion values, $\epsilon_i$, from $F_{in}$ for all web elements.

3. Calculate the expanded length, $L_i = L_{0i} + L_{0i} \cdot \epsilon_i$, of each truss component, where $L_{0i}$ is the initial length of component i.
4. Use the set of expanded lengths $\{L_i\}$ and the law of cosines to calculate the interior angles
5. Calculate the lift angle (e.g., $\lambda = 2\pi - (\theta + \phi + \psi + \sigma)$
6. Calculate truss lift by:

$$\text{Lift} = \frac{\text{span}}{2} \cos\left(\frac{\lambda}{2}\right)$$

7. Repeat steps 1-6 to generate a distribution of lift values.

FIG. 11 shows that methods according to the disclosure proved to be more effective in preventing truss uplift than the random method employed in strategy A. Strategy D proves to be the optimal strategy based on this simulation. One of ordinary skill in the art will appreciate that Strategy D may have the added benefit of increased utilization of lumber due to the fact that lumber pieces having a coefficient of linear hygroscopic expansion between about 0.08% and about 0.15% may be particularly useful for the construction of wood products requiring a certain degree of dimensional instability.

We claim:

1. A method for constructing a truss with a plurality of wood members, the method comprising:
    selecting at least a first wood member and a second wood member from a plurality of wood members, each of the first and second wood members having a value representing dimensional instability that is within a first range;
    selecting at least a third wood member from the plurality of wood members, the third wood member having a value representing dimensional instability that is within a second range that is different from the first range;
    selecting a fourth wood member from the plurality of wood members, the fourth wood member having a value representing dimensional instability that is within a third range;
    assembling a truss by using the first and second wood members having a value representing dimensional instability that is within the first range as first and second chord elements of the truss, and using the third wood member having a value representing dimensional instability that is within the second range as a web element of the truss;
    diverting the fourth wood member from the plurality of wood members as a scrap element;
    wherein the values representing dimensional instability within the first range are lower, on average, than the values representing dimensional instability within the second range;
    wherein the values representing dimensional instability within the third range are higher, on average, than the values representing dimensional instability within the first range; and
    wherein the values representing dimensional instability within the third range are higher, on average, than the values representing dimensional instability within the second range.

2. The method of claim 1 wherein the values representing dimensional instability are expansion coefficients.

3. The method of claim 2 wherein the expansion coefficients are hygroscopic or thermal.

4. The method of claim 1, further comprising:
    diverting at least a fifth wood member from the plurality of wood members as a second scrap element, the second scrap element having a value representing dimensional instability that is within a fourth range;
    wherein the values representing dimensional instability within the fourth range are higher, on average, than the values representing dimensional instability within the first range;
    wherein the values representing dimensional instability within the fourth range are lower, on average, than the values representing dimensional instability within the second range; and
    wherein the values representing dimensional instability within the fourth range are lower, on average, than the values representing dimensional instability within the third range.

5. The method of claim 2 wherein the expansion coefficients are based on each of the plurality of wood members' responses to a change in a condition.

6. The method of claim 5 wherein the condition is selected from the group consisting of: moisture, temperature, and relative humidity.

7. The method of claim 5 wherein the change may be an increase or a decrease.

8. The method of claim 1, further comprising:
    calculating a predicted uplift for the truss based on the values representing dimensional instability for each of the plurality of wood members; and
    selecting the two or more wood members as the two or more chord elements and selecting the one or more wood members as the two or more web elements based, at least partially, on the predicted uplift.

9. The method of claim 1, further comprising interconnecting the web element with at the first and second chord elements when assembling the truss.

10. A method for constructing a truss with a plurality of wood members, the method comprising:
    providing a plurality of wood members;
    predicting a value representing dimensional instability for each of the wood members in the plurality of wood members;
    calculating a predicted uplift for a truss built with wood members in the plurality of wood members based on the values representing dimensional instability for each of the plurality of wood members;
    determining a first range of values representing dimensional instability for wood members, a second range of values representing dimensional instability for wood members, and a third range of values representing dimensional instability for wood members, wherein the values representing dimensional instability within the first range are lower, on average, than the values representing dimensional instability within the second range, and wherein the values representing dimensional instability within the third range are higher, on average, than the values representing dimensional instability within the second range;

selecting a first wood member and a second wood member from the plurality of wood members, each of the first and second wood members having a value representing dimensional instability that is within the first range;

selecting a third wood member from the plurality of wood members, the third wood member having a value representing dimensional instability that is within the second range;

selecting a fourth wood member from the plurality of wood members, the fourth wood member having a value representing dimensional instability that is within the third range;

assembling a truss by using the first and second wood members as first and second chord elements of the truss and using the third wood member as a web element of the truss; and diverting the fourth wood member from the plurality of wood members as a scrap element.

11. The method of claim 10 wherein the values representing dimensional instability are expansion coefficients.

12. The method of claim 11 wherein the expansion coefficients are hygroscopic or thermal.

13. The method of claim 11 wherein the expansion coefficients are based on each of the plurality of wood members' responses to a change in a condition.

14. The method of claim 13 wherein the condition is selected from the group consisting of: moisture, temperature, and relative humidity.

15. The method of claim 14 wherein the change may be an increase or a decrease.

16. The method of claim 10, further comprising interconnecting the web element with the first and second chord elements when assembling the truss.

* * * * *